US008343423B2

(12) United States Patent
Mori et al.

(10) Patent No.: US 8,343,423 B2
(45) Date of Patent: Jan. 1, 2013

(54) AUTOMATIC ANALYZER

(75) Inventors: Hiroki Mori, Hitachinaka (JP); Yasuo Kaneko, Hitachinaka (JP); Toshihide Orihashi, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 587 days.

(21) Appl. No.: 12/336,968

(22) Filed: Dec. 17, 2008

(65) Prior Publication Data

US 2009/0214385 A1 Aug. 27, 2009

(30) Foreign Application Priority Data

Feb. 27, 2008 (JP) ................... 2008-046172

(51) Int. Cl.
*G01N 35/10* (2006.01)
(52) U.S. Cl. ................ 422/67; 422/63; 422/64; 422/65; 422/509; 422/521
(58) Field of Classification Search .................... 422/63, 422/64, 67, 509, 65, 521
See application file for complete search history.

(56) References Cited

U.S. PATENT DOCUMENTS

| 5,314,825 | A | | 5/1994 | Weyrauch et al. | |
|---|---|---|---|---|---|
| 5,320,966 | A | * | 6/1994 | Mitsumaki et al. | 436/47 |
| 5,434,083 | A | * | 7/1995 | Mitsumaki et al. | 436/48 |
| 5,741,461 | A | * | 4/1998 | Takahashi et al. | 422/67 |
| 5,876,668 | A | | 3/1999 | Kawashima et al. | |
| 6,146,592 | A | * | 11/2000 | Kawashima et al. | 422/67 |

FOREIGN PATENT DOCUMENTS

| EP | 0 825 445 A2 | 2/1998 |
|---|---|---|
| JP | 3-140844 A | 6/1991 |
| JP | 7-98320 A | 4/1995 |
| JP | 8-194004 | 7/1996 |
| JP | 8-278313 A | 10/1996 |
| JP | 2007-198986 A | 8/2007 |

\* cited by examiner

*Primary Examiner* — Jill Warden
*Assistant Examiner* — Shogo Sasaki
(74) *Attorney, Agent, or Firm* — Mattingly & Malur, PC (57) ABSTRACT

A diluted sample is reused to remeasure a sample whose measurement has been completed, which is to be manually performed. An automatic analyzer can set hold and discard conditions and manage the elapsed time after a diluted sample is pipetted. It is possible to check, before measurement is performed, whether or not each requested measurement item can be measured, and the length of time it takes before measurement of all samples is completed. The automatic analyzer has functions of: setting diluted sample hold and discard conditions; allowing an operator to specify a kind of sample, for example, to select between a parent sample and a diluted sample; separately executing pipetting or measurement; and displaying each requested measurement item for which a sample or a reagent is insufficient, and displaying the length of time it takes until measurement of all samples is completed.

12 Claims, 5 Drawing Sheets

DILUTED SAMPLE HOLD AND DISCARD CONDITIONS 3-1 ⊙ DISCARD AFTER THE COMPLETION OF AUTOMATIC REINSPECTION
3-2 ○ HOLD UNTIL DISCARD IS SPECIFIED
3-3 ○ AUTOMATIC DISCARD
3-4 ○ DISCARD A SAMPLE STARTING FROM THE OLDEST SAMPLE
3-5 ○ DISCARD AFTER THE LAPSE OF A SPECIFIED PERIOD OF TIME
SPECIFIED TIME [ 30 ] MINUTES — 3-6
3-7 ○ DISCARD AFTER MEASUREMENT SUCCEEDS (NO DATA ALARM)
3-8 ○ HOLD WHEN ITEM IS SELECTED

[CANCEL] [REGISTER]

AUTOMATIC ANALYZER

BACKGROUND OF THE INVENTION

1. Field of the Invention

The present invention relates to automatic analyzers for performing qualitative/quantitative analysis of samples such as blood and urine. The invention more particularly relates to an automatic analyzer including: a parent sample vessel holding unit for holding a parent sample; a diluted sample vessel holding unit in which a diluted sample vessel is placed, the diluted sample vessel holding a diluted sample made by diluting, with a diluent, a sample pipetted from the parent sample; and a reaction vessel in which the analysis, inspection, and measurement of the diluted sample are performed.

2. Description of the Related Art

When the analysis and inspection are performed by an automatic analyzer, a plurality of measurement items of the analysis and inspection are requested for one patient sample. Here, in the case of analysis of a very small amount of sample such as from a patient whose blood-collecting amount is limited (for example, a newborn baby and a little child), and from an experimental small animal, all requested measurement items may not be completely measured because the fluid volume is small.

As measures against the above problem, for example, JP-A-8-194004 discloses an automatic analyzer that uses a method in which a parent sample is diluted with diluent to ensure the fluid volume required for measurement items.

SUMMARY OF THE INVENTION

The above-described automatic analyzer stores, in a diluted sample vessel, a diluted sample remains after analysis and inspection to thereby meet a request for reinspection. However, after a lapse of an excessively long period of time, the diluted sample may dry and adhere to a diluted sample vessel, which leads to difficulty in washing and deterioration of the diluted sample itself. Consequently the diluted sample will become unsuitable for the qualitative/quantitative analysis and inspection.

The present invention has been made taking the above-described problems into consideration. An object of the present invention is to provide an automatic analyzer that creates few, if any, inconveniences including a case where a diluted sample becomes unsuitable for the qualitative/quantitative analysis and inspection because of the adhesion of the diluted sample due to drying, and because of the deterioration of the diluted sample.

In addition, another object of the present invention is to provide an automatic analyzer that is capable of checking, before measurement for the analysis and inspection is executed, whether or not all requested measurement items for the analysis and inspection can be completely measured, and that is capable of checking, before measurement for the analysis and inspection is executed, the time it takes before measurement of all samples is completed.

According to one aspect of the present invention, there is provided an automatic analyzer for performing the analysis and inspection of various kinds of samples including a parent sample, a diluted sample, and a combination sample in which the diluted sample and the parent sample are used in combination, said automatic analyzer comprising:

a parent sample vessel holding unit in which a parent sample vessel containing a parent sample is placed; and a diluted sample vessel holding unit in which a diluted sample vessel containing a diluted sample made by diluting the parent sample is placed;

wherein said automatic analyzer has a function of discarding, from the diluted sample vessel, the remaining diluted sample that remains after pipetting in the analysis and inspection, and holding the remaining diluted sample in the diluted sample vessel.

In addition, according to another aspect of the present invention, there is provided an automatic analyzer for performing the analysis and inspection of various kinds of samples including a parent sample, a diluted sample, and a combination sample in which the diluted sample and the parent sample are used in combination, said automatic analyzer comprising:

a parent sample vessel holding unit in which a parent sample vessel containing a parent sample is placed; and a diluted sample vessel holding unit in which a diluted sample vessel containing a diluted sample made by diluting the parent sample is placed, said automatic analyzer having a function of, before the analysis and inspection, knowing how many times and how much the analysis and inspection can be executed on the basis of the amount of the diluted sample that has been diluted.

In addition, according to the present invention, the automatic analyzer further includes a display unit for displaying, on a screen, various kinds of information about the analysis and inspection. For the analysis and inspection of the diluted sample, the estimated length of time it takes to complete the analysis and inspection of the whole requested diluted sample is displayed on the display unit.

According to the present invention, the automatic analyzer has a function of discarding, from the diluted sample vessel, the remaining diluted sample that remains after pipetting in analysis and inspection, and holding the remaining diluted sample in the diluted sample vessel. The automatic analyzer, therefore, can meet a request for remeasurement using the remaining diluted sample. If the elapsed time during which a diluted sample is held becomes too long, the diluted sample is discarded. This makes it possible to make full use of the diluted sample, and to prevent a failure of measurement for the reanalysis and reinspection from occurring which would result from the adhesion of a diluted sample to the diluted sample vessel due to drying and the deterioration of the diluted sample.

Moreover, according to the present invention, the automatic analyzer is capable of, before the analysis and inspection, knowing how many times and how much the analysis and inspection can be performed on the basis of the amount of the diluted sample that has been diluted, and is capable of displaying, on the display unit, the estimated length of time it takes to complete the analysis and inspection of the whole requested diluted sample. This enables an operator to easily handle various kinds of requested items for the analysis and inspection. As a result, the work efficiency of the operator is improved, which leads to a reduction in diagnosis time for each patient in a hospital.

BRIEF DESCRIPTION OF THE DRAWINGS

FIG. 1 is a diagram illustrating an item selection screen used to request measurement items that are displayed on a display unit included in an operation unit of an automatic analyzer according to an embodiment of the present invention;

DESCRIPTION OF THE PREFERRED EMBODIMENTS

Before the embodiments of the present invention are described in detail with reference to the drawings, some main features will be described as below.

1. For the reanalysis, reinspection, and remeasurement of a sample for which measurement has already been completed, which are to be manually performed, a situation in which the remeasurement cannot be executed due to a shortage of the sample is avoided.

More specifically, a parent sample is diluted with diluent to increase the amount of sample so that many analysis and inspection items for the reanalysis, reinspection, and remeasurement can be handled (hereinafter the analysis and inspection are also merely called "measurement"). In addition, the diluted sample is held over a period of time during which the diluted sample can be used for the analysis and inspection; and if the elapsed time during which the diluted sample is held becomes too long, the diluted sample is discarded.

2. How many times the analysis and inspection can be performed is estimated on the basis of the amount of the diluted sample before the execution of measurement. In addition, the length of time it takes to complete measurement of the whole sample can be known.

3. A display unit is used to display: an item selection screen used to request measurement of each measurement item; an analysis start screen used to start the measurement; and a pre-analysis check screen used to make a check before the measurement. Thus, the analysis and inspection can be easily performed.

First Embodiment

Figure 2:
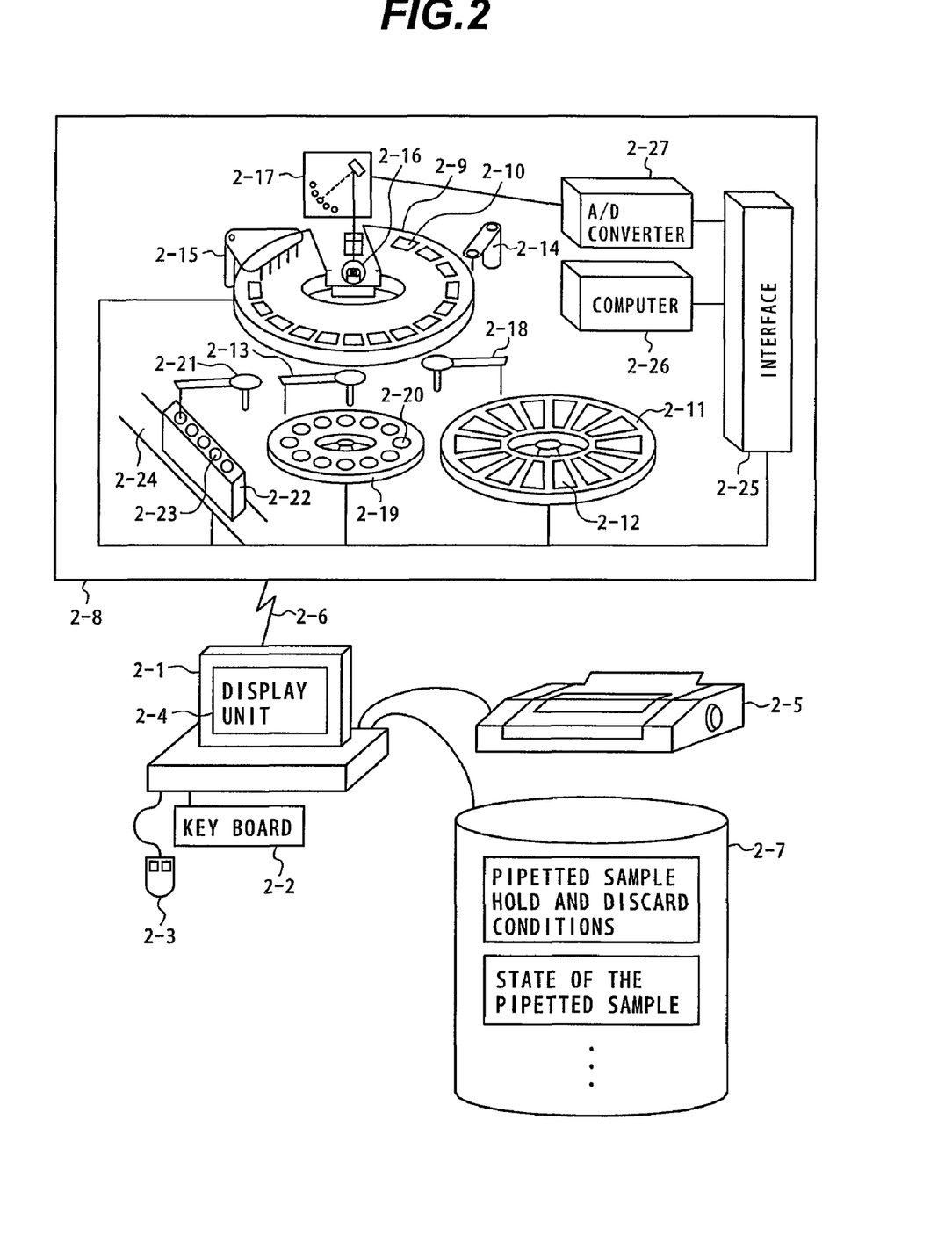
FIG. 2 is a diagram schematically illustrating the overall configuration of an automatic analyzer based on principles according to the embodiment of the present invention.

FIG. 2 is a diagram schematically illustrating the overall configuration of an automatic analyzer based on principles of the invention.

In FIG. 2, reference numeral 2-1 denotes an operation unit. The operation unit 2-1 is a computer equipped with peripheral devices. The peripheral devices are a keyboard 2-2 for inputting data; a mouse 2-3; a display unit for displaying data 2-4; a printer 2-5 for printing data; an interface 2-6 through which a connection to an analyzing unit is made; and a storage device 2-7 for storing hold and discard conditions of a diluted sample and a state of the diluted sample.

Reference numeral 2-8 denotes an analyzing unit. The analyzing unit 2-8 is connected to the operation unit 2-1 through the interface 2-6.

The analyzing unit 2-8 includes a reaction disk 2-9. A plurality of reaction vessels 2-10 are disposed along the concentric circumference of the reaction disk 2-9. Reference numeral 2-11 denotes a reagent disk. A plurality of reagent bottles 2-12 containing various kinds of reagents are disposed along the concentric circumference of the reagent disk 2-11. Around the reaction disk 2-9 are disposed a pipetting probe 2-13 for pipetting a diluted sample into the reaction disk 2-9; a mixer 2-14; a cleaning device 2-15; a light source 2-16; and a multiwavelength photometer 2-17.

A reagent pipetting probe 2-18 is disposed between the reaction disk 2-9 and the reagent disk 2-11. In addition, a diluted sample disk 2-19 is disposed at a position adjacent to the reagent disk 2-11 in such a manner that the diluted sample disk 2-19 is associated with the circumference of the rotating diluted sample pipetting probe 2-13. A plurality of diluted sample vessels 2-20, each containing a diluted sample, are located on the diluted sample disk 2-19.

The reagent disk 2-11 has the plurality of reagent bottles 2-12 thereon, each of which contains a reagent used to dilute a sample and/or a reagent used to analyze and inspect a sample.

Further, a rack transfer belt 2-24 is extended at a position adjacent to the diluted sample disk 2-19. A rack 2-22 moves along the rack transfer belt 2-24. A plurality of parent sample vessels 2-23 each containing a parent sample are placed in the rack 2-22.

A parent sample pipetting probe 2-21 is disposed between the diluted sample disk 2-19 and the rack transfer belt 2-24. The operation of the above-described mechanism is totally controlled by the computer 2-26 through the interface 2-25.

An operator uses the display unit 2-4 and the keyboard 2-2 (or the mouse 2-3) that are included in the operation unit 2-1 to give the analyzer a measurement instruction including requested measurement items. The measurement instruction is transmitted to the analyzing unit 2-8 through the interface 2-6. According to the received measurement instruction, the analyzing unit 2-8 makes measurements in the following manner.

The parent sample pipetting probe 2-21 pipettes, into the diluted sample vessel 2-20, the specified amount of parent sample contained in the parent sample vessel 2-23. On the completion of pipetting the whole amount of parent sample contained in one parent sample vessel 2-23, the rack transfer belt 2-24 moves the rack 2-22 such that the next parent sample vessel 2-23 comes to a position immediately below the parent sample pipetting probe 2-21.

On the completion of pipetting the whole amount of parent sample from all of the parent sample vessels 2-23 placed on the rack 2-22, the rack 2-22 is carried out by the rack transfer belt 2-24. During this operation, a diluent for diluting a sample contained in the diluted sample vessel 2-20 is pipetted. More specifically, the reagent pipetting probe 2-18 sucks the diluent contained in the reagent bottle 2-12, and then puts the sucked diluent into the diluted sample vessel 2-20, whereby the sample is diluted.

The diluted sample pipetting probe 2-13 pipettes the specified amount of diluted sample contained in the diluted sample vessel 2-20 into each reaction vessel 2-10 such that the required number of items is satisfied.

On the completion of pipetting the whole amount of diluted sample contained in one diluted sample vessel 2-20, the diluted sample disk 2-19 is rotated such that the next diluted sample vessel 2-20 comes at a position immediately below the diluted sample pipetting probe 2-13. The rotational operation of the reaction disk 2-9 causes the reaction vessel 2-10, into which a diluted sample has been pipetted, to rotationally move on the reaction disk 2-9.

During this operation, the reagent pipetting probe 2-18 pipets a reagent contained in the reagent bottle 2-12 into the reaction vessel 2-10 containing the sample; the mixer 2-14 stirs the reaction solution; and the multiwavelength photometer 2-17 measures the absorbance by use of the light source 2-16. After that, the cleaning device 2-15 cleans the reaction vessel 2-10 whose measurements have been completed.

The absorbance signal representing the measured absorbance is inputted into the computer 2-26 through an A/D converter 2-27 and the interface 2-25. From this absorbance signal, on the basis of an analysis method that is set beforehand for each measurement item, calibration curve data is calculated for a standard solution sample from concentration data that is set, whereas concentration data is calculated for a patient sample and a control sample from the calibration curve data obtained by the measurements of the standard solution sample.

After information obtained by symbolizing a kind of the sample is added to the thus-obtained pieces of data, they are transmitted as measurements to the operation unit 2-1 through the interface 2-6.

In the above-described operation, the display unit 2-4 and the keyboard 2-2 (and/or the mouse 2-3) are used to execute the following processing: manually remeasuring measured samples; setting diluted sample hold and discard conditions; viewing unmeasurable measurement items; and viewing the length of time it takes until measurement of the whole requested diluted sample is completed.

FIG. 1 is a diagram illustrating an item selection screen used to issue a request for measurement items.

In specification of samples to be measured 1-1, samples to be measured are selected. When an automatic selection radio button 1-2 is selected, a diluted sample is preferentially measured, and if the amount of a diluted sample is short, a parent sample thereof is used for measurement. When a manual selection radio button 1-3 is selected, three kinds of settings are available.

The first one of the settings is associated with a case where a parent sample check box 1-4 is selected. In this case, only a parent sample is used for measurement. This setting is used for first measurement, or when the parent sample residual is stored, it is used as remeasurement for measurement items for which measurements will be too low in sensitivity to make a precise measurement if a diluted sample is used for measurement.

The second one of the settings is associated with a case where a diluted sample check box 1-5 is selected. In this case, only a diluted sample is used for measurement. The diluted sample check box 1-5 can be selected only when a diluted sample is prepared and diluted sample discard conditions are not satisfied. For example, the diluted sample check box 1-5 is used for measurement of an additional measurement item, and for remeasurement of a measurement item for which no trouble is caused in measurement even if a diluted sample is used for measurement.

The third one of the settings is associated with a case where both the parent sample check box 1-4 and the diluted sample check box 1-5 are selected. In this case, both a parent sample and a diluted sample are used. The third setting is used for, for example, a case where the amount of a diluted sample is not sufficient although the second setting is satisfied.

Figure 3:
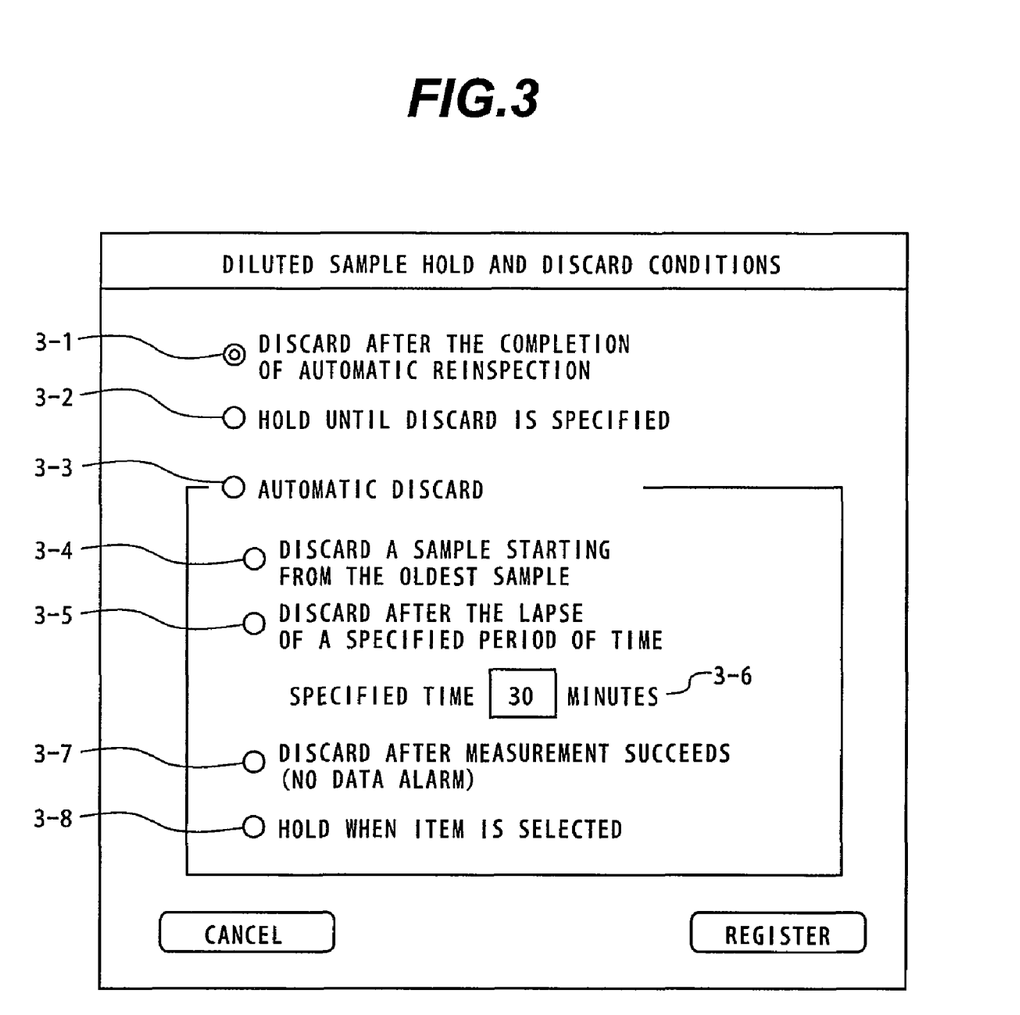
FIG. 3 is a diagram illustrating a diluted sample hold and discard conditions setting screen according to the embodiment of the present invention.

Pressing a diluted sample button 1-6 displays a diluted sample hold and discard conditions setting screen shown in FIG. 3. This button is used to perform three kinds of settings of diluted sample hold and discard conditions.

The first one of the settings of diluted sample hold and discard conditions is associated with a case where a radio button 3-1 is selected for discarding a diluted sample after the completion of automatic reinspection. According to the first setting, a diluted sample is discarded after first measurement is executed and automatic reinspection of the first measurement is completed. In this case, remeasurement of the diluted sample cannot be carried out.

The second one of the settings is associated with a case where a radio button 3-2 is selected for holding a diluted sample until its discard is specified. According to the second setting, a diluted sample is held until the diluted sample is discarded based on discard specification to be performed on a pre-analysis check screen (shown in FIG. 4). The second setting is used when an operator determines timing at which a diluted sample is to be discarded.

The third one of the settings is associated with a case where a radio button 3-3 is selected for automatically discarding a diluted sample. Several discard conditions can be set in the third setting. When a radio button 3-4 is selected for discarding a sample starting from the oldest one, a diluted sample is automatically discarded starting from the oldest one such that a diluted sample vessel is empty and thereby trouble is not caused in measurement by the automatic analyzer. When a radio button 3-5 is selected for discarding a diluted sample after the lapse of a specified period of time, a diluted sample for which the specified time inputted into a specified time edit box 3-6 has elapsed is automatically discarded.

This makes it possible to prevent a sample, which has been degraded due to the lapse of time, from being measured. Thus, the reliability of measurements can be increased.

In addition, when a check box 3-7 is selected for discarding a diluted sample after measurement succeeds, a sample is discarded after all requested measurement items succeed. When a check box 3-8 is selected for holding a diluted sample when item is selected, if a requested measurement item remains unmeasured, a sample is not discarded even if discard conditions are satisfied. The use of these condition settings makes it possible to flexibly handle discarding operations of a diluted sample.

Because diluted sample selection settings can be made irrespective of before or after the operation of the automatic analyzer, diluted samples are adapted for various kinds of operation modes.

Figure 4:
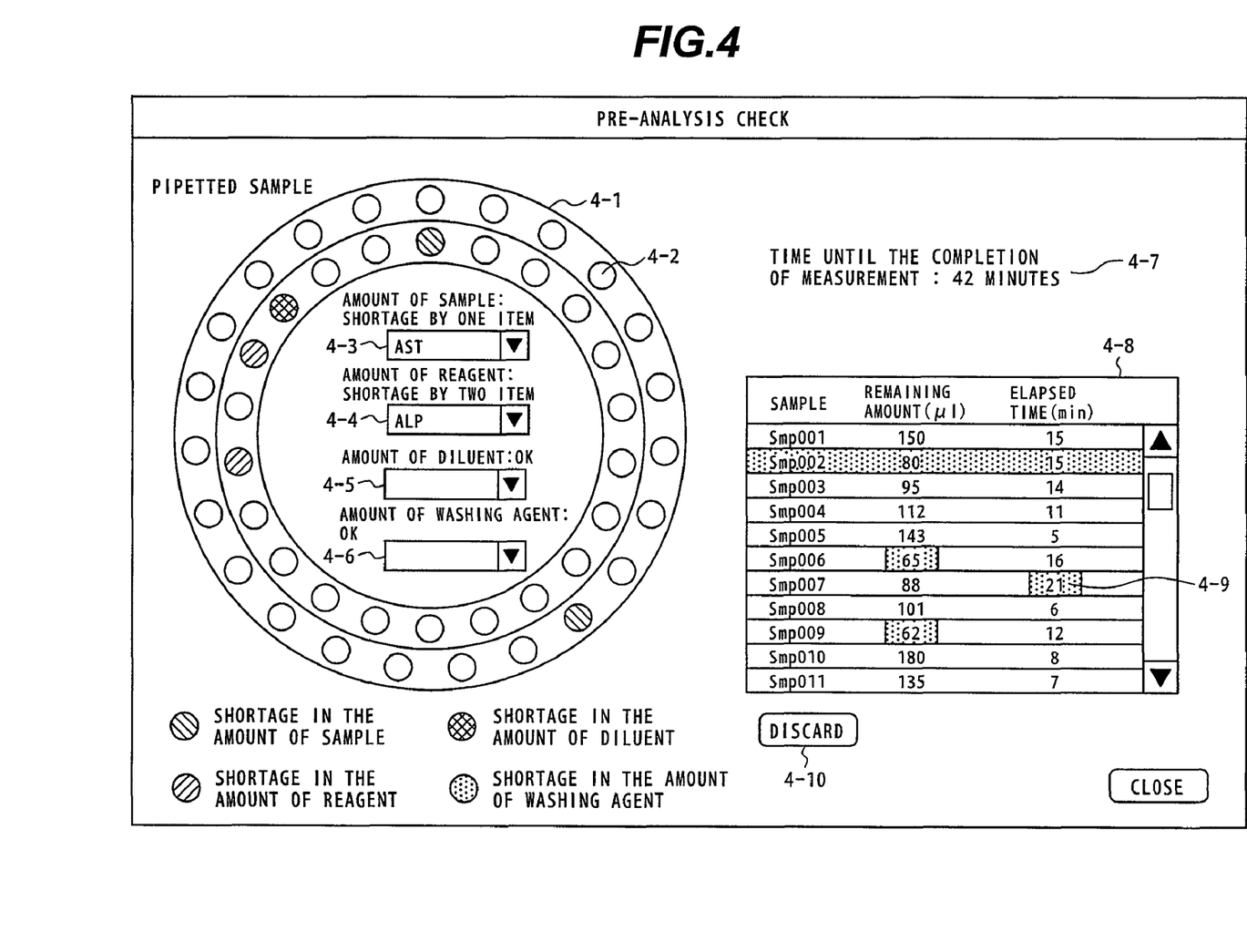
FIG. 4 is a diagram illustrating a pre-analysis check screen used to check before measurement whether or not each diluted sample can be measured according to the embodiment of the present invention.

FIG. 4 is a diagram illustrating a pre-analysis check screen. By use of the pre-analysis check screen, it is possible to know, before the start of measurement, whether or not requested measurement items can be measured, and to know the length of time it takes until all measurements are completed. An indication 4-1 schematically shows a pipetted sample disk having concentric rings which hold diluted sample vessels, while an indication 4-2 schematically shows a diluted sample vessel. The indications 4-2 expressing diluted sample vessels are disposed on the pipetted sample disk 4-1. With the pre-analysis check screen, if the amount of diluted sample, the amount of reagent to be used, the amount of diluent, or the amount of washing agent is insufficient, they are highlighted with color and patterns in accordance with the causes of insufficiency as shown in FIG. 4.

In addition, when a diluted sample vessel 4-2 is selected, measurement item names for which measurement cannot be performed are listed based on the amount of diluted sample, the amount of reagent, the amount of diluent, the amount of washing agent, and a requested measurement item, which are known at present.

A combo box 4-3 showing an amount of sample lists names of measurement items for which measurement cannot be performed due to the shortage in the amount of diluted sample. A combo box 4-4 showing an amount of reagent lists names of measurement items for which measurement cannot be performed due to the shortage in the amount of reagent. A combo box 4-5 showing an amount of diluent lists names of measurement items for which measurement cannot be performed due to the shortage in the amount of diluent. A combo box 4-6 showing an amount of washing agent lists names of measurement items for which measurement cannot be performed due to the shortage in the amount of washing agent.

The above-described combo boxes allow an operator to eliminate causes for which a sample cannot be subjected to measurement before the execution of the measurement, or to accept or reject each measurement item.

Moreover, the length of time it takes until measurement of all samples is completed is displayed by a measurement-completion time text 4-7. The remaining amount and the elapsed time after pipetting are displayed by a pipetted sample list box 4-8 for a diluted sample for each diluted sample. When the remaining amount is to be displayed, the insufficient remaining amount is highlighted with a different color 4-9. Likewise, when the elapsed time is to be displayed, the elapsed time which has passed the discard specification time is highlighted with a different color 4-9.

Further, when the pipetted sample list box 4-8 for a diluted sample is selected and then a discard button 4-10 is selected, a diluted sample can be discarded.

Figure 5:
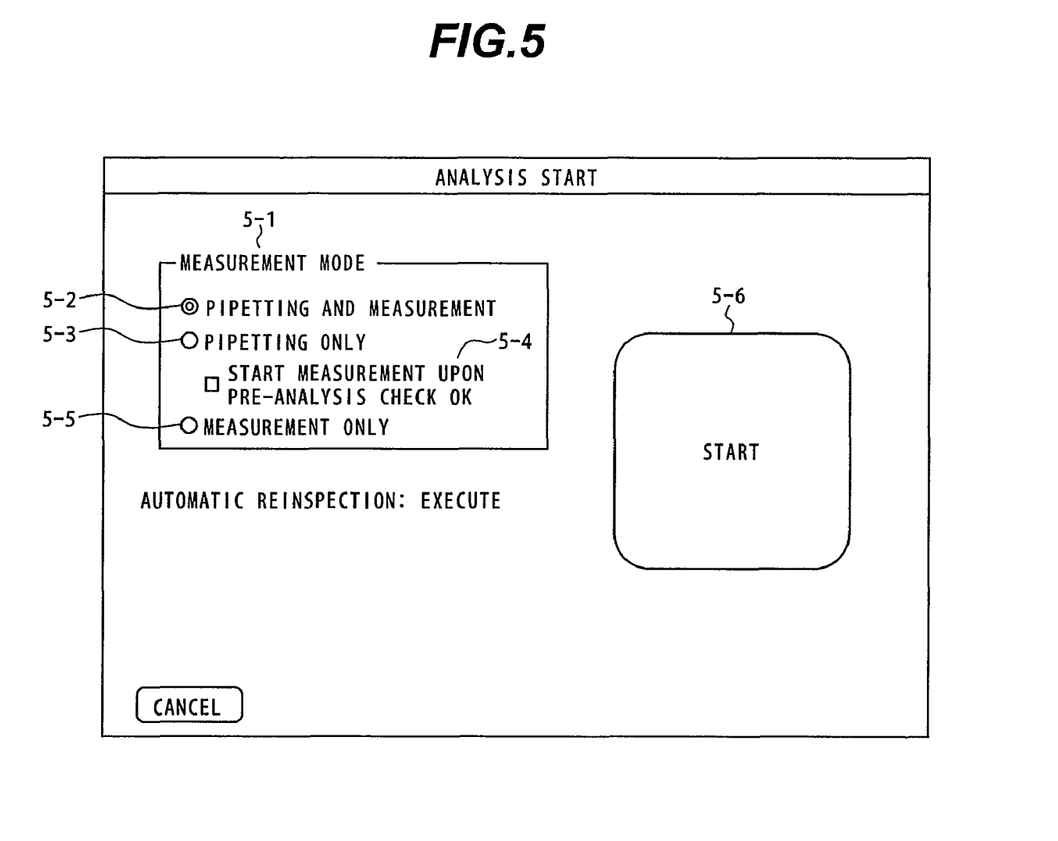
FIG. 5 is a diagram illustrating an analysis start screen used to start measurement of samples such as a diluted sample according to the embodiment of the present invention.

FIG. 5 is a diagram illustrating an analysis start screen. The analysis start screen is used to specify the start of measurement. In measurement mode 5-1, a mode can be selected from among the following three modes.

A first mode is associated with a case where a pipetting and measurement radio button 5-2 is selected. The first mode is a mode in which both pipetting from a parent sample and measurement are executed.

The second mode is associated with a case where a pipetting-only radio button 5-3 is selected. The second mode is a mode in which only pipetting from a parent sample is executed.

When a start button 5-6 is selected to execute only pipetting of the diluted sample from the parent sample in the second mode, it becomes possible to make a check in the pre-analysis check screen shown in FIG. 4 even in first measurement. If a check box 5-4 for starting measurement upon pre-analysis check OK is selected, measurement can be automatically started when all measurement items are judged to be measured by the pre-analysis check.

The third mode is associated with a case where a measurement-only radio button 5-5 is selected. The third mode is a mode in which only measurement is executed. The measurement may be executed after the check and adjustment performed on the pre-analysis check screen shown in FIG. 4.

In the above-described embodiment, the diluted sample vessels are located in the diluted sample vessel holding unit. However, vessels included in a reaction disk or a reagent disk may also be used for a diluted sample vessel. In addition, vessels may be circularly placed in two or three layers on a reaction disk with diluted sample vessels and reaction vessels placed in combination.

The present invention can be used for a wide range of automatic analyzers, each of which is capable of handling a diluted sample, capable of measuring a plurality of items for a sample, and capable of holding a sample pipetted from a parent sample.

What is claimed is:
1. An automatic analyzer comprising:
a plurality of reaction vessels, a plurality of parent sample vessels, a plurality of reagent vessels, and a plurality of diluted sample vessels;
a rotatable reaction disk for rotating said reaction vessels arranged on said reaction disk about an axis of said reaction disk, each of said reaction vessels receiving a sample and a reagent;
a photometer for measuring a sample received in one of said reaction vessels on said reaction disk;
a parent sample vessel holding unit for holding said parent sample vessels, each of which receives a parent sample;
a reagent disk on which said reagent vessels are arranged, each of said reagent vessels receiving a dilution reagent used to dilute a sample or an analysis reagent used to analyze a sample;
a rotatable diluted sample disk for rotating said diluted sample vessels arranged on said diluted sample disk about an axis of said diluted sample disk, each of said diluted sample vessels receiving a diluted sample diluted from a parent sample by a dilution reagent;
a parent sample pipetting probe for dispensing a parent sample into said diluted sample vessel arranged on said diluted sample disk from said parent sample vessel arranged on said parent sample vessel holding unit;
a reagent pipetting probe for dispensing a diluted reagent into said diluted sample vessel arranged on said diluted sample disk from said reagent vessel arranged on said reagent disk;
a diluted sample pipetting probe for dispensing a diluted sample into said reaction vessel from said diluted sample vessel arranged on said diluted sample disk, and said diluted sample pipetting probe sucking out a diluted sample from said diluted sample vessel and discarding said diluted sample;
an operation unit having a display unit configured to display a conditions setting screen including diluted sample hold and discard conditions, said conditions setting screen configured to set items to be measured by said photometer with respect to said samples and said analysis reagents, said conditions setting screen configured to apply measurement instructions for said photometer with respect to said samples and said analysis reagents, and said conditions setting screen configured to set a timing for discarding a specific diluted sample from said diluted sample vessel on said diluted sample disk; and
a control unit configured to control rotation of said reaction disk and said photometer to analyze and inspect a sample in accordance with said measurement instructions from said operation unit, said control unit further configured to control rotation of said diluted sample disk and said diluted sample pipetting probe to suck out said specific diluted sample from said diluted sample vessel on said diluted sample disk by said diluted sample pipetting probe and to discard said sucked specific diluted sample at said timing set with said conditions setting screen.

2. The automatic analyzer according to claim 1, wherein said display unit is further configured to display a screen for selecting and setting to discard or to hold the diluted sample irrespective of a time of starting operation of the automatic analyzer.

3. The automatic analyzer according to claim 1, wherein the samples selected for analysis and inspection include a diluted sample, a parent sample and a combination sample which is a combination of the diluted sample and the parent sample which are provided on the reaction disk by the parent sample pipetting probe, diluted sample pipetting probe and reagent pipetting probe under the control of said control unit.

4. The automatic analyzer according to claim 1, wherein said display unit is further configured to display information including an elapsed time of analysis and a remaining amount of individual diluted samples on said diluted sample disk.

5. The automatic analyzer according to claim 1, wherein said display unit and said control unit are further configured to specify said diluted sample vessel which contains said specific diluted sample to be discarded from among said diluted sample vessels arranged in said diluted sample vessel holding disk.

6. The automatic analyzer according to claim 4, wherein said display unit is further configured to display an estimated length of time until completion of the analysis and inspection of the entirety of a requested diluted sample.

7. The automatic analyzer according to claim 1, wherein said display unit is further configured to display information of whether or not an amount of sample, an amount of analysis reagent, an amount of dilution reagent, and an amount of washing agent are sufficient for the completion of all the requested analyses and inspection of a specific diluted sample.

8. The automatic analyzer according to claim 1, wherein said display unit is further configured to display a plurality of buttons for selecting various kinds of samples for analysis and inspection, the various kinds of samples including a diluted sample, a parent sample, and a combination sample which is a combination of the diluted sample and the parent sample, the various kinds of samples being provided on the reaction disk by the parent sample pipetting probe, diluted sample pipetting probe and reagent pipetting probe under the control of said control unit, and wherein the diluted sample is to be selected on the conditions that the diluted sample exists, and that discarding of the diluted sample is not set.

9. The automatic analyzer according to claim 6, wherein said display unit is further configured to display, on a pre-analysis check screen different from said conditions setting screen, various kinds of information about the analysis and inspection, and wherein for the analysis and inspection of the requested diluted sample, the estimated length of time it takes to complete the analysis and inspection of the entirety of the requested diluted sample is displayed on said display unit.

10. The automatic analyzer according to claim 1, wherein the reaction disk has a cleaning device having a washing agent for cleaning the reaction vessels after analysis and inspection, wherein said display unit is further configured to display, on a pre-analysis check screen different from said conditions setting screen, various kinds of information about the analysis and inspection, and wherein for the analysis and inspection of the diluted sample, whether or not an amount of sample, an amount of analysis reagent, an amount of dilution reagent, an amount of the washing agent are sufficient for the completion of all the requested analysis and inspection, is displayed on said display unit using characters, colors, and marks.

11. The automatic analyzer according to claim 1, wherein the reaction disk has a cleaning device having a washing agent for cleaning the reaction vessels after analysis and inspection, wherein said display unit is further configured to display a plurality of buttons for specifying an automatic start of the analysis and inspection, when an amount of sample, an amount of analysis reagent, an amount of dilution reagent and an amount of the washing agent are sufficient for the completion of all the requested analysis and inspection and the pipetting operation of pipetting from said specified parent sample vessel into said diluted sample vessel is completed.

12. The automatic analyzer according to claim 2, wherein said display unit is further configured to display information including an elapsed time and a remaining amount of the diluted sample.

* * * * *